US007665348B2

(12) United States Patent
Giles

(10) Patent No.: US 7,665,348 B2
(45) Date of Patent: Feb. 23, 2010

(54) SYSTEM AND METHOD FOR DETERMINING ATOMIZATION CHARACTERISTICS OF SPRAY LIQUIDS

(75) Inventor: Durham Kenimer Giles, Davis, CA (US)

(73) Assignee: Arena Pesticide Management, Inc., Davis, CA (US)

( * ) Notice: Subject to any disclaimer, the term of this patent is extended or adjusted under 35 U.S.C. 154(b) by 274 days.

(21) Appl. No.: 11/743,780

(22) Filed: May 3, 2007

(65) Prior Publication Data

US 2008/0307893 A1 Dec. 18, 2008

Related U.S. Application Data

(62) Division of application No. 11/104,287, filed on Apr. 12, 2005, now Pat. No. 7,278,294.

(51) Int. Cl.
*G01N 29/02* (2006.01)

(52) U.S. Cl. ....................... 73/64.53; 73/53.01; 73/592; 73/861.18; 239/61; 239/72

(58) Field of Classification Search ................ 73/64.53, 73/53.01
See application file for complete search history.

(56) References Cited

U.S. PATENT DOCUMENTS

| | | | |
|---|---|---|---|
| 4,328,025 | A | 5/1982 | Whitcomb |
| 4,823,268 | A | 4/1989 | Giles et al. |
| 4,905,897 | A | 3/1990 | Rogers et al. |
| 5,134,961 | A | 8/1992 | Giles et al. |
| 5,389,781 | A | 2/1995 | Beck et al. |
| 5,442,552 | A | 8/1995 | Slaughter et al. |
| 5,544,813 | A | 8/1996 | Giles et al. |
| 5,653,389 | A | 8/1997 | Henderson et al. |
| 5,704,546 | A | 1/1998 | Henderson et al. |
| 5,763,873 | A | 6/1998 | Beck et al. |
| 5,809,440 | A | 9/1998 | Beck et al. |
| 5,833,144 | A | 11/1998 | Kinter |
| 5,841,035 | A | 11/1998 | Andoh et al. |
| 5,861,556 | A | 1/1999 | Nukui et al. |
| 5,881,919 | A | 3/1999 | Womac et al. |
| 5,908,161 | A | 6/1999 | Womac et al. |
| 5,967,066 | A | 10/1999 | Giles et al. |

(Continued)

OTHER PUBLICATIONS

"Sensing Spray Nozzle Vibration as a Means for Monitoring Operation", by D.K. Giles, pp. 1-7, ILASS Americas, 17th Annual Conference on Liquid Atomization and Spray Systems, Arlington, VA, May 2004.

(Continued)

*Primary Examiner*—Hezron Williams
*Assistant Examiner*—Rodney T Frank
(74) *Attorney, Agent, or Firm*—Dority & Manning, P.A.

(57) ABSTRACT

A system and method for determining the atomization characteristics of fluids being emitted by a nozzle is disclosed. In one embodiment, a fluid is emitted through a nozzle while simultaneously sensing vibrations occurring within the nozzle. The vibrations provide information about the atomization characteristics of the fluid. By comparing the sensed vibrations to vibration patterns produced by known fluids through the same or a similar nozzle, the atomization characteristics of the fluid being tested can be predicted. In one embodiment, for instance, the atomization characteristics of a fluid may be determined as a function of velocity or flow rate through the nozzle.

17 Claims, 14 Drawing Sheets

(a) side view (b) front / side view

U.S. PATENT DOCUMENTS

| | | | |
|---|---|---|---|
| 6,003,383 | A | 12/1999 | Zielinska et al. |
| 6,053,053 | A | 4/2000 | Huotari |
| 6,170,338 | B1 | 1/2001 | Kleven et al. |
| 6,237,425 | B1 | 5/2001 | Watanobe |
| 6,260,941 | B1 | 7/2001 | Su et al. |
| 6,276,218 | B1 | 8/2001 | Waers |
| 6,595,035 | B1 * | 7/2003 | Maley ...................... 73/19.03 |
| 6,596,996 | B1 | 7/2003 | Stone et al. |
| 6,689,338 | B2 | 2/2004 | Kotov |
| 7,278,294 | B2 * | 10/2007 | Giles et al. ................. 73/64.53 |
| 7,311,004 | B2 * | 12/2007 | Giles .......................... 73/592 |
| 2005/0000277 | A1 * | 1/2005 | Giles .......................... 73/120 |
| 2005/0076818 | A1 | 4/2005 | Grimm et al. |
| 2006/0265106 | A1 | 11/2006 | Giles et al. |

OTHER PUBLICATIONS

Abstract of Article—Breakup length of forced liquid jets, Kalaaji et al., Physics of Fluids, vol. 15, Issue 9, Sep. 2003, pp. 2469-2479.

Abstract of Article—Controlling droplet deposition with polymer additives, Bergeron et al., Nature, vol. 405(6788), Jun. 15, 2000, pp. 772-775.

Abstract of Article—Design Factors affecting Spray Characteristics and Drift Performance of Air Induction Nozzles, Ellis et al, Biosystems Engineering, vol. 82, Issue 3, Jul. 2002, pp. 289-296.

Abstract of Article—Designing intelligent fluids for controlling spray applications, Bergeron, C. R. Physique, vol. 4, Issue 2, Mar. 2003, pp. 211-219.

Abstract of Article—Different Modes of Vortex Shedding: An Overview, Zdravkovich, Journal of Fluids and Structures, vol. 10, Issue 5, Jul. 1996, pp. 427-437.

Abstract of Article—Effects of formulation on spray nozzle performance for applications from ground-based boom sprayers, Miller et al., Crop Protection, vol. 19, Issues 8-10, Sep. 12, 2000, pp. 609-615.

Abstract of Article—How adjuvants influence spray formation with different hydraulic nozzles, Ellis et al., Crop Protection, vol. 18, Issue 2, Mar. 1999, pp. 101-109.

Abstract of Article—Instrumentation and start up of a new elongational rheometer with a preshearing history, Rios et al., Review of Scientific Instruments, vol. 73, Issue 8, Aug. 2002, pp. 3007-3011.

Abstract of Article—Mixing Characteristics of a Flapping Jet from a Self-Exciting Nozzle, Mi et al., Applied Scientific Research, vol. 67, No. 1, 2001, pp. 1-23.

Abstract of Article—Modification of a vortex street by a polymer additive, Cressman et al., Physics of Fluids, vol. 13, Issue 4, Apr. 2001, pp. 867-861.

Abstract of Article—On vortex shedding behind a circular disk, Miau et al., Experiments in Fluids, vol. 23, No. 3, Jul. 1993, pp. 225-233.

Abstract of Article—Optimization of acoustic signals in a vortex-shedding flowmeter using numerical simulation, von Lavante, et al., International Journal of Heat and Fluid Flow, vol. 20, Issue 4, Aug. 1999, pp. 402-404.

Abstract of Article—Pulsed-jet Microspray Applications for High Spatial Resolution of Deposition on Biological Targets, Downey et al., Journal of the International Institutes for Liquid Atomization and Spray Systems, vol. 14, Issue 2, 2004, 17 pages.

Abstract of Article—Squeezing flow viscometry for nonelastic semi-liquid foods—theory and applications, Campanella et al., Crit. Rev. Food Sci. Nutr., vol. 43, No. 3, 2002, pp. 241-264.

Abstract of Article—Suppression of Aerosol Generation During Spraying and Deposition of Consumer Products, Giles et al., Journal of the International Institutes for Liquid Atomization and Spray Systems, vol. 15, Issue 4, 2005, pp. 423-438.

Abstract of Article—Utility Adjuvants, McMullan, Weed Technology, vol. 14, No. 4, 2000, pp. 792-797.

Abstract of Article—Vortex Shedding from Bluff Bodies and a Universal Strouhal Number, Nakamura, Journal of Fluids and Structures, vol. 10, No. 2, Feb. 1996, pp. 159-171.

Abstract of Article—Vortex-Induced Vibrations of an Elastic Circular Cylinder, Zhou et al., Journal of Fluids and Structures, vol. 13, Issue 2, Feb. 1999, pp. 165-189.

Article—Break-up dynamics and drop size distributions created from spiraling liquid jets, Wong et al., International Journal of Multiphase Flow, vol. 30, 2004, pp. 499-520.

Article—Non-Newtonian viscous oscillating free surface jets, and a new strain-rate dependent viscosity form for flows experiencing low strain rates, Bechtel et al., Rheol Acta, vol. 40, 2001, pp. 373-383.

Piezo Film Sensors Technical Manual from Measurement Specialties, Inc., Appendices A and B, Apr. 1999, pp. 59-82.

Presentation—Spray Deposition and Drift From Two "Medium" Nozzles, Hoffman et al., at the 2002 Joint ASAE/NAAA Technical Meeting, Reno, NV. Paper No. 02-AA04. St. Joseph, MI. ASAE.

Product Data Sheet for AIM Command® Spray System (Case IH), 2 pages.

Article—A new model to determine dynamic surface tension and elongated viscosity using oscillating jet measurements, Bechtel et al., J. Fluid Mech., vol. 293, 1995, pp. 379-403.

Article—Effects of spray adjuvants on swath patterns and droplet spectra for a flat-fan hydraulic nozzle, Chapple et al., Crop Protection, vol. 12, No. 8, 1993, pp. 579-590.

Article—Measurement of Extensional Viscosity of Polymer Solutions and its Effects on Atomization from a Spray Nozzle, R. W. Dexter, Atomization and Sprays, vol. 6, 1996, pp. 167-191.

Article—Optimal Control of Vortex Shedding Using Low-Order Models. Part I—Open-Loop Model Development, Graham et al., Int. J. Numer. Meth. Engng., vol. 44, 1999, pp. 945-972.

Article—Optimal Control of Vortex Shedding Using Low-Order Models. Part II—Model-Based Control, Graham et al., Int. J. Numer. Meth. Engng., vol. 44, 1999, pp. 973-990.

Article—Aerial Spray Drift from Different Formulations of Glyphosate, I. W. Kirk, Transactions of the ASAE, vol. 43, No. 3, pp. 555-559.

Article—A System for Determining Dynamic Surface Tension Using the Oscillating Jet Technique, Reichard, et al., Atomization and Sprays, vol. 7, 1997, pp. 219-233.

Paper No. AA03-002 entitled Field Comparisons for Drift Reducing/Deposition Aid Tank Mixes, Wolf, et al., for presentation at the 2003 ASAE/NAAA Technical Session, Dec. 8, 2003.

Paper No. 03-1060 entitled Spray Mix Adjuvants for Spray Drift Mitigation—Progress Report, I. W. Kirk for presentation at the 2003 ASAE Annual International Meeting, Jul. 27-30, 2003.

Paper No. 01-1102 entitled Spray Drift Estimates from Aerial Spray Droplet Spectra, I. W. Kirk for presentation at the 2001 NAAA/ASAE Joint Technical Session, Dec. 3, 2001.

Paper entitled A Summary of Tank Mix and Nozzle Effects on Droplet Size by Spray Drift Task Force, 2001, 5 pages.

* cited by examiner

Power spectra of liquid flow through an XR11004 fan nozzle @ 40 psi. Legend: Blue = water Red = syrup Black = water+detergent (a) side view (b) front / side view Ethyl alcohol results Glycerin results

SYSTEM AND METHOD FOR DETERMINING ATOMIZATION CHARACTERISTICS OF SPRAY LIQUIDS

RELATED APPLICATIONS

The present application is a Divisional Application of U.S. patent application Ser. No. 11/104,287 filed on Apr. 12, 2005.

BACKGROUND OF THE DISCLOSURE

The performance of spraying systems, as measured by the droplet size spectra and distribution pattern of the spray is highly dependent on the fluid properties of the liquid being sprayed. The classic fluid properties such as density, equilibrium surface tension, dynamic surface tension, shear viscosity, extensional viscosity, void fraction of incorporated gasses, etc., all affect the behavior of the liquid as it passes through an atomizer, and subsequently, the characteristics of the resulting spray. When sprays are produced for coating, drying and other processes, the spray characteristics are critical factors in the performance of the process and using the spray and the resulting quality of the product.

To achieve desired spray characteristics, the proper nozzle or atomizer must be selected and the optimal operating conditions of the atomizer and fluid handling system must be determined for the fluid to be atomized. Selection of the nozzle and determination of the operating conditions can be an extensive, iterative, experimental process due to the complexity of the fluid-atomizer interaction. Especially for complex fluids that are heterogeneous, non-Newtonian or otherwise difficult to characterize, a priori predictions of sprayer performance can be difficult and inaccurate. Subsequent changes in the fluid composition, wear in the atomizer or other departures from the original test conditions can require repeat experiments.

Laboratory measurements of fluid properties can be tedious, expensive and time consuming. Additionally, the measurements are often made using standardized techniques that do not closely approximate the conditions in the actual spraying process. These conditions can include turbulence in the flow system, shear rates during flow and atomization, spatial and temporal gradient in temperature, reactions in the fluid, etc.

Likewise, the measurement of spray characteristics such as droplet size spectra, spatial distributions and patterns and droplet velocities requires specialized, expensive equipment and technical expertise in proper sampling in data interpretation. With limited feedback on atomizer performance, especially in processes where the sprays or products are not visible to system operators, generation of poor quality sprays with undesirable characteristics is often undetected until adverse consequences have occurred.

While these challenges are present for any spraying applications, a particular problem exists for agricultural spraying where the spray fluids can be mixtures of pesticides, fertilizers, surfactants, shear-inhibitors, buffers, adhesives and other supplemental agents known as spray adjuvants. These mixtures are highly variable and often created for specific fields to be treated; the physical properties of these mixtures are very complex and it is difficult to predict how the fluid mixtures will behave in a given spray system.

Spray drift, or the inadvertent movement of small spray droplets from the target site to a non-target area, is a significant issue presently facing agricultural applicators throughout the United States. The strongly related issues of spray quality, that is, coverage of the target and efficacy of the product against the target pests are also of great concern. Agricultural applicators desire to use the best drift management methods and equipment to provide the safest and most efficient applications of pest control materials to the targeted pest. They are responsible for making good decisions in the field on a daily basis. Spray droplets that drift off-site or are not correctly applied to the target crop or pest represent wasted time, resources and result in environmental pollution. This results in increased costs for the crop grower and, subsequently, to the consumer. In addition, materials such as herbicides and defoliants that drift off-site can result in a serious financial liability if surrounding crops are damaged.

The minimization of off-site movement of agricultural sprays is to the benefit of all concerned—applicators, farmers, regulators, the public and the environment. Applicators need additional methods and equipment to balance or optimize spray tank adjuvant performance and economics to achieve drift mitigation goals for a given application. In particular, a need currently exists for an apparatus and method for assisting applicators in determining the best possible application parameters to help meet product instructional label criteria and mitigate spray drift. It has long been understood that spray droplet size is the most important variable in spray coverage, performance and spray drift control or mitigation. For an agricultural spray dispensed from an aircraft, spray nozzle selection is the first factor considered when attempting to influence the spray droplet spectrum. Second are the operational factors that influence atomization. These include nozzle angle or deflection to the airstream, aircraft speed, and spray liquid pressure. Spray tank additives or adjuvants play an auxiliary role in spray droplet spectra. There are currently over 416 adjuvants marketed in California alone according to Crop Data Management Systems (Marysville, Calif.). Adjuvants are classified as surfactants, spreaders, stickers, deposition aids, activators, humectants, antifoamers, wetting agent, and drift reduction agents. These agents are added to the spray tank mix that may include a number of active ingredients in the pesticide formulations. Adjuvants can aid in the product making better contact with the pest by spreading it over the leaf surface or the body of the insect pest. Adjuvants can also reduce the likelihood of the product dripping off the leaf onto the ground. Similarly, excessive or incorrect adjuvant use can cause the product to drip or run off the leaf. Adjuvants also can be very useful in helping the product "stick" to the leaf or crop, preventing runoff during rain or irrigation. Finally, adjuvants are often marketed as drift reduction agents. The addition of an appropriate adjuvant can tend to increase droplet size, which generally reduces driftable fines. Unfortunately for applicators, sometimes recommended mixtures are found to be "poor combinations", even if applied under "ideal climatic conditions", when damage to crops, crop losses and drift problems are experienced.

Droplet size is determined by the physical properties of the components of the droplet fluid—in this case, the tank mix, usually composed of water, pesticide active ingredient formulations and adjuvant(s). The key properties of the tank mix that have a significant effect on droplet size and the resulting atomization profile are: dynamic and equilibrium surface tension, extensional viscosity, and shear viscosity. Each time the applicator adds something to the tank mix, the physical properties of that tank mix change and that changes the atomization profile. Because of the continued development and advancements in adjuvants, a need also exists for a system and method for assisting applicators in making sound decisions about the addition of these products and the subsequent impact their addition will have on the actual application, both for spray quality and for drift potential.

What is needed by all applicators, not just aerial but also for field crop boom applicators and orchard and vineyard air carrier applicators, is a field method to estimate the atomization characteristics of particular spray mixes that they are about to apply, especially if the mix is used only occasionally. By knowing the atomization characteristics of the mix, one can then choose the proper nozzle and spray conditions to avoid drift and optimize deposit and efficacy. One may even, upon getting the information, decide to delay an application until better environmental conditions exist.

In a broader sense beyond pesticide spraying, optimizing any spraying system requires that the atomizing properties of the fluid be known. The complexity of fluid properties and the complexity of the fluid-nozzle interaction make the prediction of the atomizing properties from laboratory measurements of individually-measured fluid properties (e.g., dynamic and equilibrium surface tension, shear viscosity, extensional viscosity, density, etc.) difficult and inaccurate. The difficulty of selecting and conducting the most appropriate laboratory tests of the fluid properties, combined with the uncertainty of prediction models of droplet size spectra from the resulting measurements, lead to the need for a more direct and simple method for the end user to determine atomization characteristics of a fluid before undertaking a spray operation.

SUMMARY OF THE DISCLOSURE

The present disclosure is directed toward a system and method to characterize the atomization properties of fluids in order to select, optimize, maintain and control the proper nozzle and spray conditions to achieve a desired spray with specified properties. Additionally, the system may be used to determine if changes in a fluid mixture will produce significant changes in the fluid behavior as it passed through an atomizer. By characterizing the atomization properties of fluids, the present disclosure allows a user to control droplet size and droplet spectra in order to minimize drift and to assist in applying the fluid onto a target site.

In one embodiment, the system of the present disclosure can include an orifice or nozzle similar or identical to a spray nozzle to be used for spraying. The fluid is excited by being forced through the nozzle under a controlled pressure or controlled flowrate and the resulting vibrations of the fluid sheet or jet are detected by a sensor. The sensor is in communication with a controller that determines the characteristics of the vibration. These characteristics can include the magnitude of the vibrations, the directions of the vibration, the spectral composition of the vibrations, the transmission of the vibrations through the fluid or combinations of the characteristics. In one embodiment, the sensed characteristics of a fluid to be tested are compared to the characteristics measured for a fluid of known composition and atomization properties. The relative atomization properties are then determined.

In one embodiment, the test orifice and the flowrate of the test fluid are adjusted to approximate known atomization regimes such as those shown in FIG. 1. The flow rates and orifice diameters are adjusted to cover a working range of the dimensionless numbers, Reynolds (Re), Weber (We) and Ohneserge (Oh), that define the fundamental map of atomization. ($Re=Dv\rho/\mu$; $We=Dv^2\rho/\sigma$; $Oh=We^{1/2}/Re$ where $D$=characteristic diameter, $v$=characteristic velocity, $\rho$=fluid density, $\mu$=fluid viscosity and $\sigma$=fluid surface tension). When fluid properties are unknown, these numbers can be estimated from a priori knowledge or approximated with values from similar fluid.

In one embodiment, a positive displacement pump is in communication with the controller and is adjusted to vary the fluid flow rate through the orifice in a programmed sequence, representing a range of fluid velocities through the orifice. The microcontroller receives the vibration data from the sensor simultaneously and determines the fluid vibration properties as a function of the liquid velocity and flowrate through the orifice.

In general, the method of the present disclosure for determining the atomization characteristics of a fluid being emitted by a nozzle includes the steps of first emitting a fluid from a nozzle at controlled conditions. Vibrations occurring within the fluid nozzle are then sensed while the fluid is being emitted. The sensed vibrations are then compared to the vibrations of a known fluid having known atomization properties for determining the relative atomization properties of the fluid being emitted from the nozzle. The controlled conditions at which the fluid is emitted from the nozzle may include a known flow rate, temperature, pressure, and the like. The controlled conditions can be known by placing various sensors within the fluid flow path. For instance, the system may include a flow meter, one or more temperature sensors, and one or more pressure sensors that are each placed in communication with a controller that also receives the sensed vibrations in determining the relative atomization properties of the fluid. The controller may be, for instance, one or more microprocessors.

In one embodiment, the method may include the step of sensing a fluid pressure drop over an orifice while the fluid is being emitted from the nozzle. The pressure drop may be communicated to a controller for determining a fluid shear viscosity and a density of the fluid. The orifice over which the pressure drop is sensed may comprise the nozzle itself or may be positioned upstream from the nozzle.

In addition to sensing fluid pressure over an orifice, a fluid pressure drop may also be sensed over a tortuous path through which the fluid flows. The tortuous path may be positioned upstream from the nozzle and, in one embodiment, may comprise a packed bed. By sensing the pressure drop over the tortuous path, a fluid extensional viscosity may be determined.

In one embodiment, the vibrations that are sensed from the nozzle are converted into a spectral density that is used to determine a power spectrum. The power spectrum is then compared to the power spectrum of one or more reference fluids for determining the relative atomization properties of the fluid. For example, in one embodiment, the sensed vibrations are compared to the vibrations of a plurality of known fluids. The known fluids may include, for instance, a relatively low viscosity fluid, a relatively high viscosity fluid, and a fluid having a viscosity in between the relatively low viscosity fluid and the relatively high viscosity fluid.

Once the relative atomization properties of the fluid are determined, one can select a nozzle and operating conditions for emitting the fluid from the selected nozzle in a fluid application process as desired. Basically, the atomization properties of the fluid may be determined for any suitable process in which the fluid is to be emitted from a nozzle. In one particular embodiment, for instance, the atomization properties of the fluid are determined for applying the fluid in an agricultural process. The fluid, for instance, may comprise a pesticide, an herbicide, a fertilizer, or any other similar material. In agricultural processes, for example, the fluid may be emitted from a nozzle that is mounted to a boom that is in turn pulled by a tractor or may be emitted by a nozzle mounted to an aircraft.

In general, any suitable device may be used in order to sense the nozzle vibrations as the fluid is being emitted from the nozzle. For example, in one embodiment, an accelerometer may be used. The accelerometer may sense vibrations in a single direction or in multiple directions.

In one embodiment, the fluid is emitted through the nozzle and into a spray chamber. An optical device, such as any suitable camera, may be used to optically inspect a flow pattern being emitted by the nozzle. The flow pattern may be further used to characterize the atomization characteristics of the fluid.

DETAILED DESCRIPTION

In general, the present disclosure is directed to a system and process for determining the atomization properties of complex fluids without the need for direct measurement of physical properties or spray droplet size spectra, spray pattern or droplet velocities. More particularly, in one embodiment, the fluid to be characterized is pumped through an orifice and the resulting vibration of the fluid flow is measured by a sensor. In one embodiment, the pressure drop of the fluid across the test orifice is simultaneously measured in order to provide an estimate of the shear viscosity of the fluid and the pressure drop across a tortuous path, such as across a packed bed of screens, is measured in order to provide an indication of the extensional viscosity.

In one embodiment, the system may be designed to be sufficiently simple and small so that sprayer operators in industries such as agricultural field spraying can use the system in field conditions using only a small sample of the spray fluid to be dispensed. After characterization of the fluid, they can select the optimal spray nozzle or operating conditions to produce the desired spray characteristics. For example, they may use the system to test a spray liquid mixture composed of various components in order to select a nozzle to minimize spray drift during application to a field. It should be understood, however, that in addition to agricultural applications, the method and system of the present disclosure may be used to characterize and determine the atomization properties of fluids in any suitable process in which the fluid is to be emitted from a nozzle. For example, in one embodiment, the method and system of the present disclosure may be incorporated into a paint spraying operation.

Figure 1:
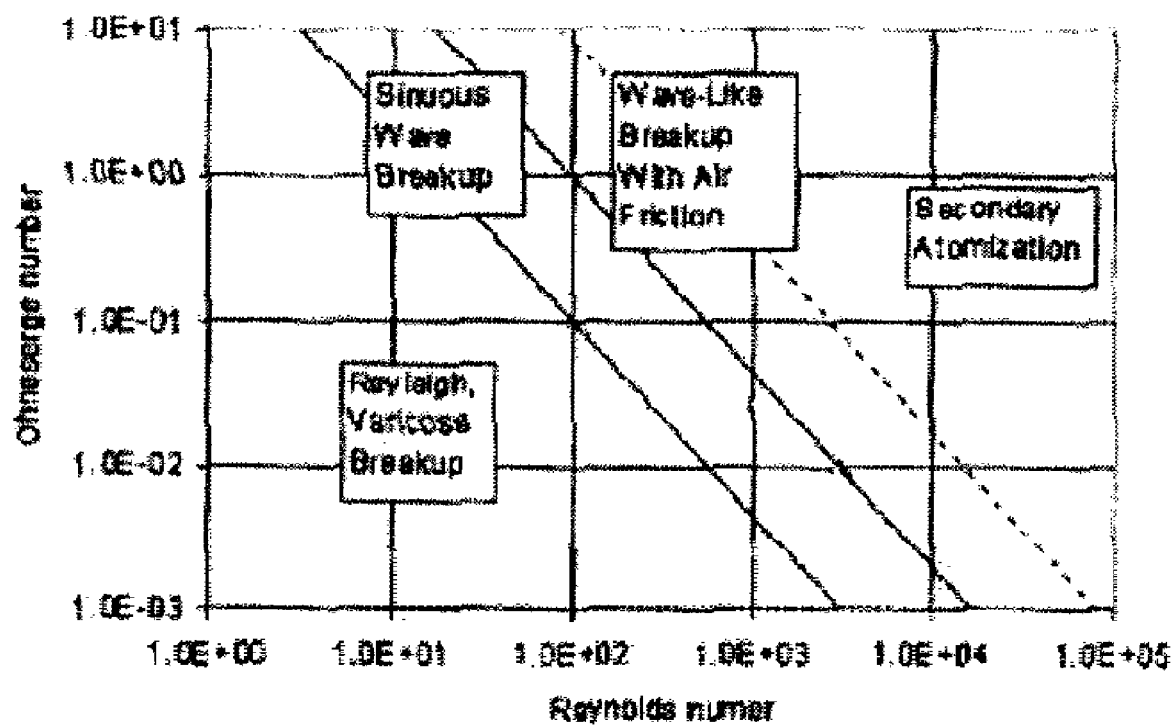
FIG. 1 is the classic map of liquid atomization regimes showing predominant mode of breakup versus the orifice flow nondimensional numbers, Re and We.
Figure 2:
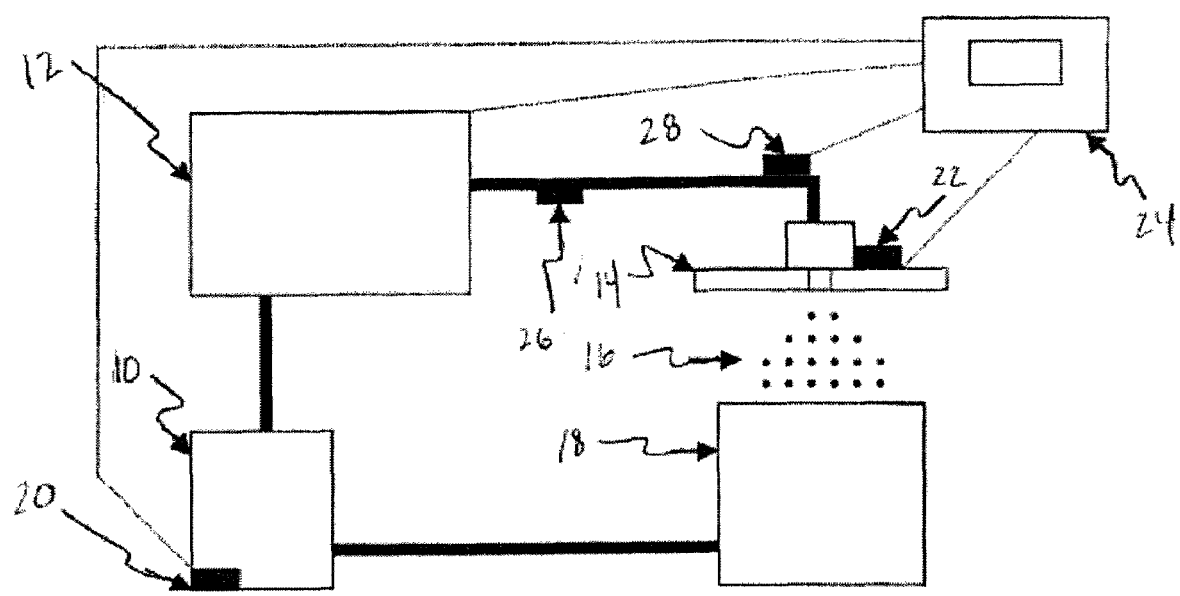
FIG. 2 is a plan view of one embodiment of a system made in accordance with the present disclosure.

Referring to FIG. 2, one embodiment of a system made in accordance with the present disclosure is shown. As illustrated, the system includes a supply reservoir 10 in which the fluid to be tested is contained. In general, any suitable fluid may be tested in accordance with the present disclosure. The fluid, for instance, may contain various ingredients including suspended particles. Further, the fluid may be adapted for use in any process as desired. For example, in one embodiment, the fluid may comprise a pesticide, herbicide or fertilizer that is to be applied during an agricultural spray process. In an alternative embodiment, the fluid may comprise a fuel. For instance, the present disclosure may be used to characterize the atomization properties of fuels when the fuels are being injected into an engine.

The fluid contained in the supply reservoir 10 is pumped from the supply reservoir in this embodiment by a pumping device 12. In general, any suitable pumping device may be used. In one embodiment, for instance, the pumping device 12 may comprise a positive displacement pump that is capable of pumping the fluid from the supply reservoir in controlled amounts. As shown in FIG. 2, the fluid contained in the supply reservoir is pumped through a test nozzle 14 to produce a sheet, jet or spray 16 that may optionally be collected in a collection reservoir 18.

In order to ensure that the fluid is pumped through the system at a controlled temperature, the supply reservoir may be placed in communication with a temperature control unit 20 that is configured to maintain the fluid at a specified temperature. Alternatively, a temperature sensor may be placed within the system in order to simply know the temperature of the fluid as it is being emitted by the nozzle 14.

In accordance with the present disclosure, a vibration sensor 22 is placed in association with the nozzle 14 for sensing vibrations within the nozzle as the fluid is being emitted by the nozzle.

The vibration sensed by the vibration sensor 22 can provide much information about the properties of the fluid and specifically the atomization properties of the fluid being emitted by the nozzle. For instance, it is known that flowing fluids that interact with structures or nozzles produce characteristic vibrations. The fundamental process is the periodic separation of the boundary layer of flow passed any structure with sufficiently bluff trailing edges. The fluid properties of surface tension (dynamic and equilibrium) and viscosity (shear and extensional or elongational) affect the behavior of the fluid flow and breakup. Of particular significance, the vibrational frequencies that are sensed along with certain vectors of the vibration provide flow rate and droplet size information about the fluid as it is emitted from the particular nozzle.

In general, any suitable fluid nozzle may be monitored according to the present disclosure. For instance, the fluid nozzle may emit a fan-type spray pattern or a conical spray pattern. Different nozzles will emit certain frequencies of vibration. Thus, the reference nozzle should generally be similar to the test nozzle.

In addition to testing different types of nozzles, both continuously flowing fluid nozzles and pulsed fluid nozzles may be used in the system and process of the present disclosure. When used in conjunction with pulsed nozzles, the vibration analysis is capable of separating vibrations due to atomization properties from vibrations due to pulsation.

Examples of nozzles that may be used as test nozzles in the system of the present disclosure include metering orifice plates that are commercially available from the TeeJet Company. The orifice plates are available in a range of sizes from 0.008 inches to 0.250 inches in diameter. The metering plates represent an abrupt, sharp orifice. Straight stream nozzles may also be used and are available from the Spraying Systems Company. Such straight stream nozzles are available in orifice diameters of from 0.041 inches to 1.375 inches and provide a smooth flow transition prior to the orifice. In still another embodiment, fan nozzles may be used to produce liquid sheets. Industrial fan nozzles are available in fan angles of 15°, 25°, 40°, 50°, 65°, 73°, 80°, 95°, 110°, and the like. The fan nozzles can have an equivalent orifice diameter of 0.011 inches to 1.375 inches.

Air inclusion nozzles may also be used. Air inclusion nozzles produce a more complex flow passageway and are commonly used in the ground application industry. Air inclusion nozzles typically produce vibration profiles that have an amplitude approximately two orders of magnitude greater than conventional nozzles. Air inclusion nozzles are also sensitive to flow conditions such as nozzle clogging.

When testing fluids for agricultural spray applications, typically the spray nozzles include fan nozzles that have flow angle ranges from 400 to 1100 and flow ranges from about 0.1 gallons per minute to 1.0 gallons per minute (at 40 psi standard pressure).

In one embodiment, flow conditioning sections may be incorporated into the system in order to produce low turbulence as the fluid enters the nozzle area. Flow conditioning can be as simple as a straight section of smooth tube or may include more orifice diameters upstream of the nozzle. Alternatively, an array of straightening tubes constructed of, for instance, thin wall stainless steel tubing, can be packed to create more laminar flow section prior to nozzle.

Referring to FIG. 3, one exemplary embodiment of a fan nozzle 30 that may be used as a test nozzle in accordance with the present disclosure is shown. Nozzle 30 as illustrated in FIG. 3 is a typical nozzle used in agricultural applications.

As also illustrated in FIG. 3, a vibration sensor 32 is mounted on the nozzle for sensing vibrations. Various different types of vibration sensors may be used in accordance with the present disclosure. For example, in one embodiment, an accelerometer may be used. The vibration sensor may be configured to sense vibrations in a single direction, or in multiple directions, such as triaxial accelerometers.

When sensing vibrations in multiple directions, it has been discovered that each direction may provide different information regarding the properties of the fluid and/or the properties of the nozzle. As shown in FIG. 3, as used herein, the Z-axis or direction comprises the direction of flow of a fluid through the nozzle. For instance, if the nozzle is pointing downward, the Z-axis comprises a vertical line. The X-axis, on the other hand, is perpendicular to the Z-axis and extends to the left and right of the nozzle when facing a front of the nozzle. The remaining axis, the Y-axis, is perpendicular to the Z-axis and to the X-axis. When sensing vibrations, the Y-axis typically provides information related to atomization and spray quality. The Z-axis provides information related to flow rate, while the X-axis provides information related to pulse valve operation when the valve is pulsating.

Some examples of vibration sensors that may be used in the present disclosure include any suitable accelerometer including piezoelectric films.

Referring back to FIG. 2, the vibration sensor 22 may be placed in any appropriate location on the nozzle 14 for sensing vibrations. For instance, the vibration sensor 22 can be placed on the nozzle housing or, alternatively, can be otherwise incorporated into the body of the nozzle. In some applications, it has been found that the vibration sensor can also be placed upstream from the nozzle and still be capable of registering vibration frequencies.

Once the vibration sensor 22 measures vibrations from the fluid nozzle 14, the signal created by the sensor is fed to a controller 24 for analysis. The controller 24 may comprise, for instance, a microprocessor or a plurality of microprocessors. The controller 24, for instance, may be used to determine peak vibration, duration of vibration and the spectral composition of the vibration. In one embodiment, for instance, the signal created by the vibration sensor 22 can be manipulated and conditioned. For example, the nozzle vibration can be measured and a spectral analysis, such as a Fast Fourier Transform, is conducted to determine a power spectrum. The power spectrum can then be analyzed and compared to the power spectrum of a reference fluid that has known atomization properties. In this manner, the atomization properties of the fluid being fed through the system can be determined.

In one particular embodiment, for instance, the controller 24 may store the atomization properties of multiple fluids that each have different viscosities. For instance, the controller may include the atomization characteristics of a reference fluid having a relatively low viscosity, a reference fluid having a relatively high viscosity, and a reference fluid that has a viscosity in between the relatively low viscosity fluid and the relatively high viscosity fluid. Of course, the atomization characteristics of many other fluids may be stored within the microprocessor 24. By comparing the vibration patterns of the fluid being emitted by the nozzle 14 to the known atomization properties of the reference fluids, relatively accurate estimations can be made regarding droplet size and/or the spray pattern of the fluid as a function of flow rate and process conditions.

As shown in FIG. 2, the system of the present disclosure can further include a flow meter 26 and one or more pressure sensors 28. The flow meter may be placed in communication with the controller in order to provide the controller with the flow rate of the fluid being emitted through the nozzle 14. As also shown, the controller 24 may be used to control and receive information from various other components in the system. For instance, the controller 24 may receive information and control the pumping device 12 and may receive information or control the temperature control unit 20.

The pressure sensor 28 as shown in FIG. 2 may also be in communication with the controller 24. The pressure sensor 28 in one embodiment, may determine the pressure drop of the fluid across the nozzle 14. When coordinated with the pumping device 12, the pressure drop versus flow rate information provides an estimate of the fluid shear viscosity and density independently from the fluid vibration data.

Instead of measuring the pressure drop across the nozzle 14, in an alternative embodiment, an orifice may be positioned upstream from the nozzle 14. The pressure sensor 28 may determine the pressure drop against the orifice for also determining fluid shear viscosity and density.

In still another embodiment of the present disclosure, this system can include a tortuous path positioned in between the supply reservoir 10 and the fluid nozzle 14. The tortuous path, for instance, may comprise a packed bed, such as a packed bed of screens. An additional pressure sensor may be positioned to determine the pressure drop of the fluid over the tortuous path. When coordinated with the pumping device 12 and/or the flow meter 26, the pressure drop over the tortuous path versus flow rate information provides an estimate of the fluid extensional viscosity independently from the fluid vibration data.

When the system includes the pressure sensor 28 as shown in FIG. 2, as described above, information from the pressure sensor and the flow meter 26 may be used in conjunction with the geometry of the nozzle 14 to characterize the shear viscosity of the fluid. A simple equation relating flow rate of a fluid through an orifice to the pressure drop through the orifice is $m=C_d A_t (2\rho\Delta p/)^{1/2}$ where m=mass flowrate, $C_d$ is a drag coefficient related to the fluid and the orifice characteristics and $A_t$ is a characteristic of the test nozzle 14, $\Delta p$=the measured pressure drop across the orifice and $\rho$=the density of the fluid. The $C_d$ term is a function of Reynolds Number (Re=Dvρ/μ where D=characteristic diameter, v=characteristic velocity, ρ=fluid density and μ=fluid viscosity). When the test nozzle 14 is installed, the orifice characteristics are known. Therefore, knowing the flowrate from the flowmeter and the pressure drop across the orifice from the pressure sensor, a term for the fluid density and viscosity can be calculated using iteration. This information can be used in characterizing the fluid, especially when considered in conjunction with the vibration data from flow through the orifice.

As described above, in one embodiment, the vibration information received from the vibration sensor may be converted into a power spectrum for comparison to the power spectrum of various reference fluids under similar conditions. For many nozzles, such as especially nozzles used in the agricultural industry, the nozzles produce characteristic vibrations in the range of from about 4 kHz to about 6 kHz bands. In general, a higher power spectrum indicates better atomization and usually smaller droplet size.

In one embodiment, the pumping device 12 as shown in FIG. 2 may be configured to vary the flow rate of the fluid being tested in a programmed sequence. For instance, the controller 24 may be placed in communication with the pumping device 12 for varying the flow rate in a predetermined manner. By varying the flow rate in a programmed sequence, vibrations generated by the fluid flowing through the nozzle can be determined as a function of velocity. In this manner, the atomization properties of the fluid can be determined also as a function of velocity and/or flow rate with respect to the test nozzle.

In addition to the vibration sensor 22 as shown in FIG. 2, the system can further include an optical sensor positioned to observe the spray pattern 16 that is emitted from the nozzle 14. In general, any suitable optical sensor may be used, such as an array of LED lights in conjunction with light sensors, or may comprise one or more cameras. The optical sensor may be configured to inspect the spray or sheet 16 being emitted from the nozzle to determine or measure the shape of the spray. For instance, a narrow spray width may indicate larger droplet size. This information can then be used in conjunction with the information received from the vibration sensor.

The present disclosure may be better understood with respect to the following examples.

Example No. 1

Figure 3:
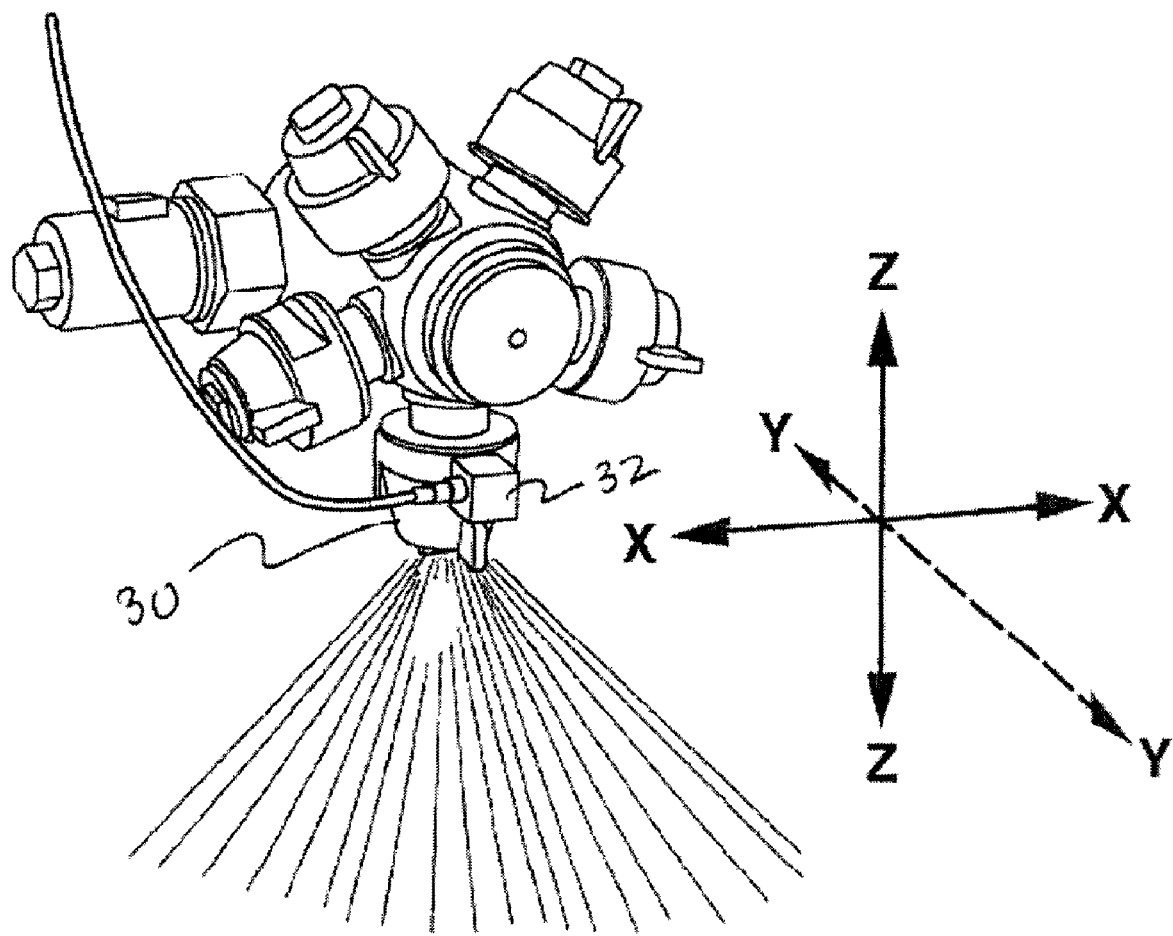
FIG. 3 is a perspective view of one embodiment of a vibration sensor attached to a nozzle for use in accordance with the present disclosure.

A number of fluids were sprayed through a TeeJet XR11004 fan nozzle. The fan nozzle tested had a 110° flow angle which refers to the extent of the fan-like shape within the X-Z axis plane. The nozzle also had a 0.4 gallon per minute flow rate at 40 psi liquid supply pressure. Fluid was supplied to the nozzle at 40 psi (276 kPa). A single chip accelerometer (Analog Devices ADXL 311) was mounted on the nozzle body to sense the vibration along the axis normal to the fan (the "Y" axis as shown in FIG. 3). Data were collected for 2 seconds and a Discrete Fourier Transform was performed on the data by an on-board microprocessor to produce the power spectrum of the signal.

Figure 4:
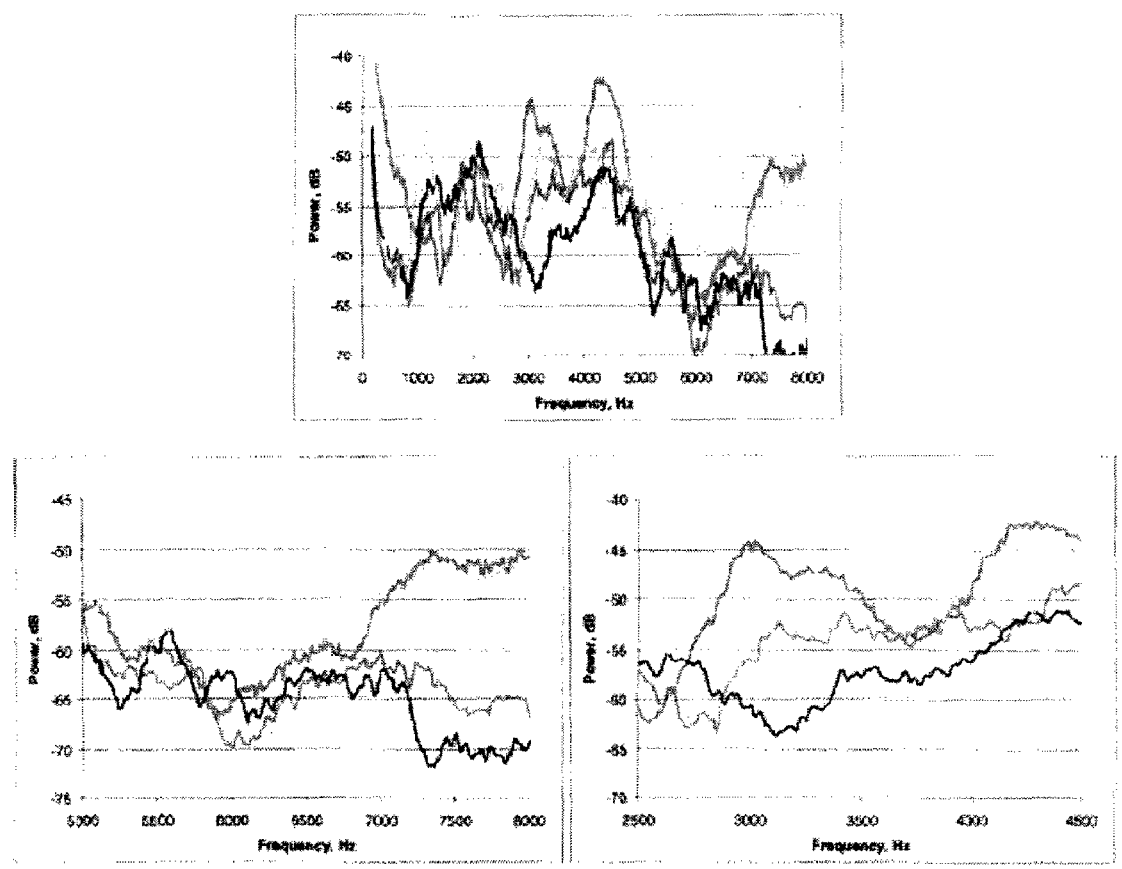
FIG. 4 is a graphical representation of the results obtained in Example 1.

Results for tap water, a viscous fluid (thick sugar syrup), a low surface tension fluid (water+1% dishwashing detergent) and a fluid with polymer-like properties (fat free salad dressing—with guar gum and other thickeners) are shown in FIG. 4. Differences in the spectra for the fluids were apparent, especially in the 2.5-4.5 and 5-8 kHz frequency bands and when considering that the dB response axis is a log scale.

As shown by the results in FIG. 4, a relationship does exist between frequency and viscosity of fluids being emitted by a nozzle.

Example No. 2

Figure 5:
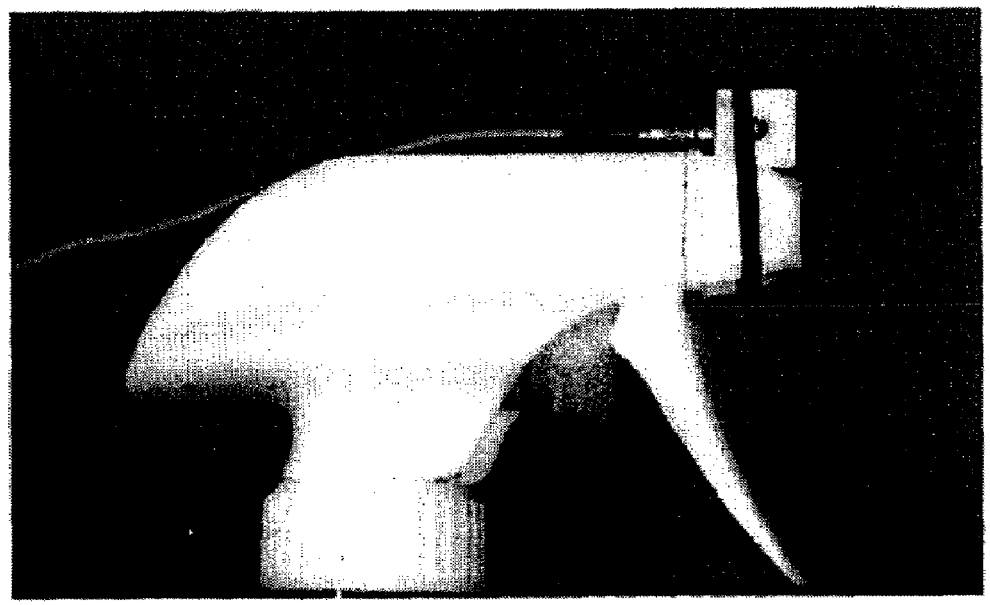
FIGS. 5A and B represent a side view and a perspective view of the nozzle tested according to Example 2 below.
Figure 5:
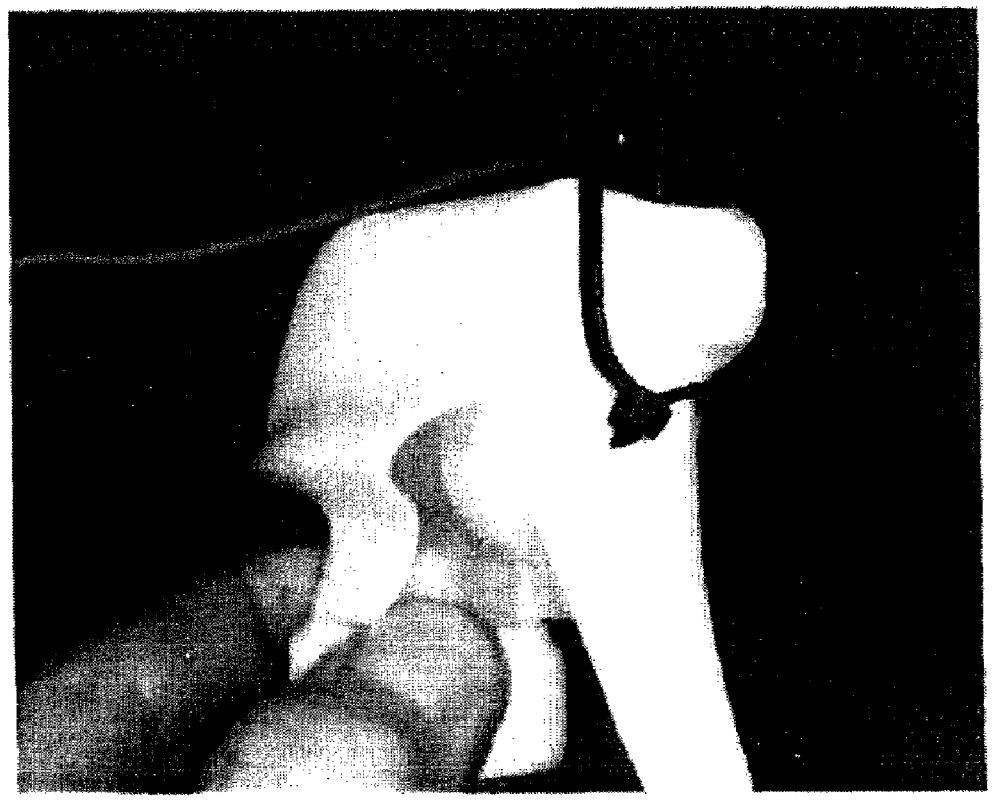

The potential simplicity and an inexpensive embodiment of the disclosure were demonstrated using a manually-actuated piston pump and close-coupled spray nozzle as shown in FIG. 5. A triaxial accelerometer (PCB Model 356A22) was coupled to the outlet of the spray nozzle. The integrated pump was a positive displacement piston pump that dispensed 0.8 ml/stroke. The nozzle was a fixed orifice producing a hollow cone spray. Four fluids were tested to determine the vibration characteristics and the resulting spray droplet size, as visualized by adding a dye to the spray liquid and photographing the spray deposit.

Figure 6:
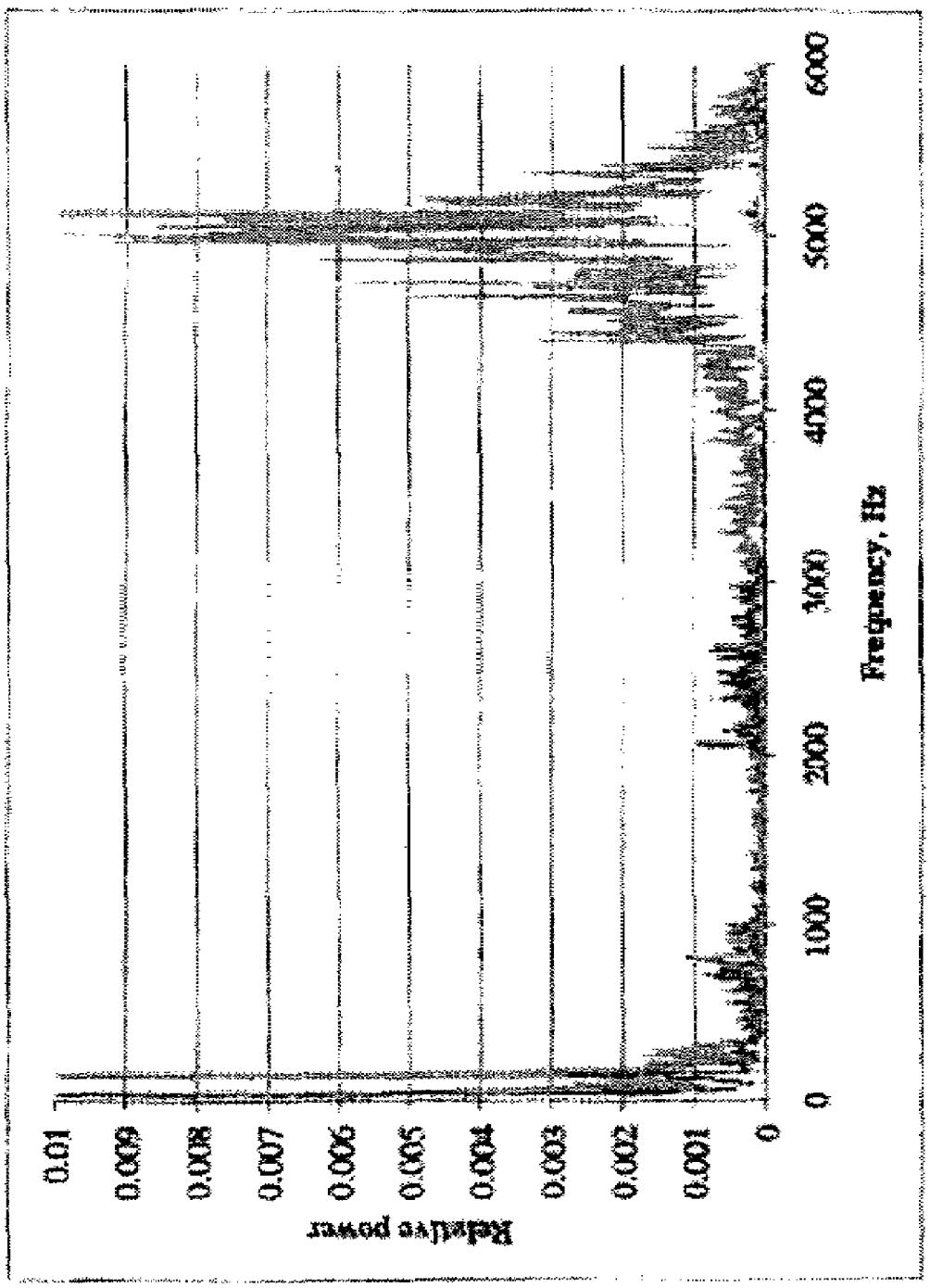
FIGS. 6-14 are graphical representations of the results obtained in Example 2.
Figure 7:
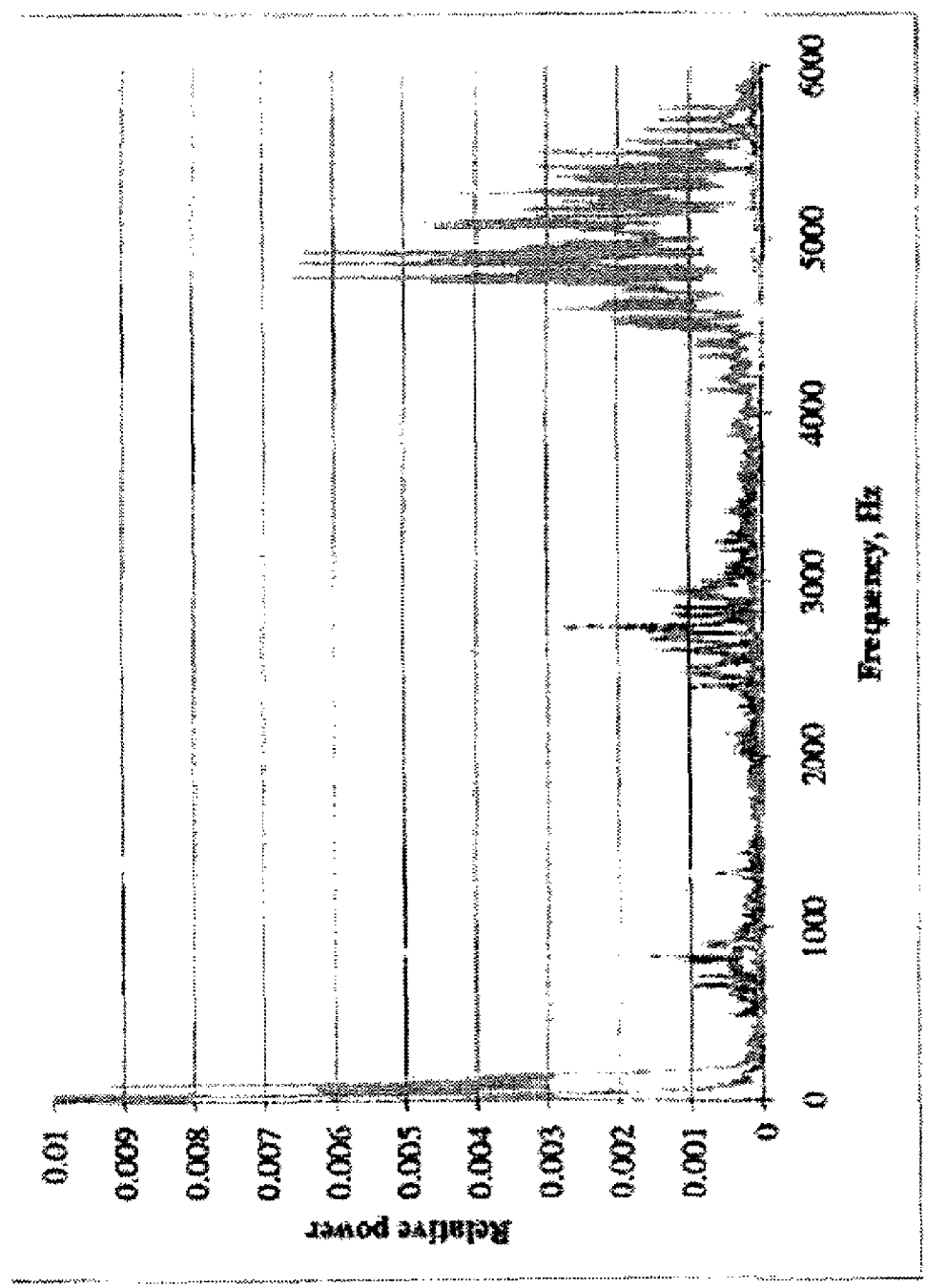
Figure 8:
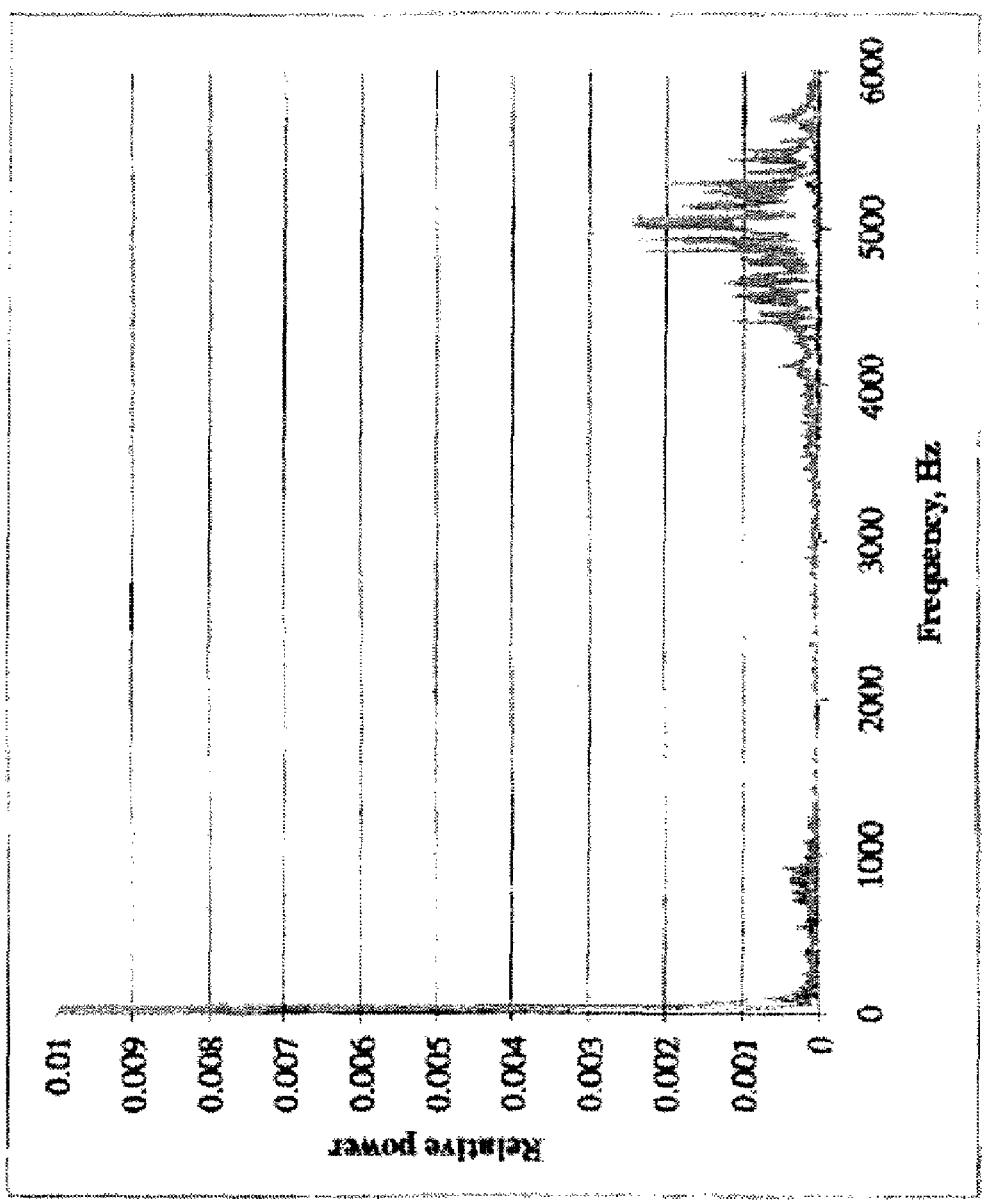
Figure 9:
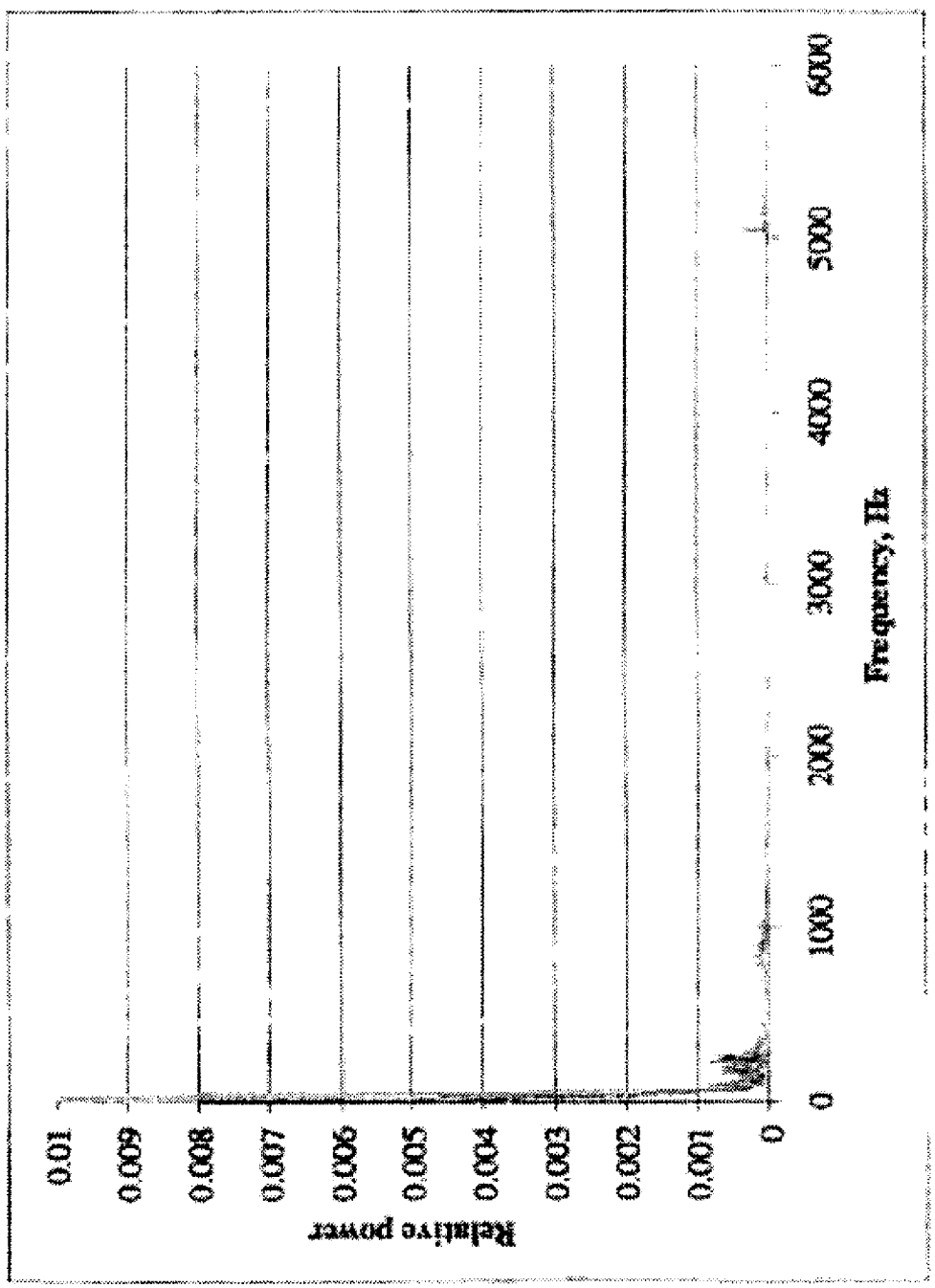

The reference fluid was municipal water. The test fluids were 40% ethyl alcohol, a commercial spray surface cleaner (Formula 409) and glycerin. Results for water appear in FIG. 6; results for ethyl alcohol appear in FIG. 7; results for the spray cleaner appear in FIG. 8; and results for glycerin appear in FIG. 9. A clear relationship between the relative power in the 4-6 kHz frequency band and the resulting spray droplet size was observed.

Figure 10:
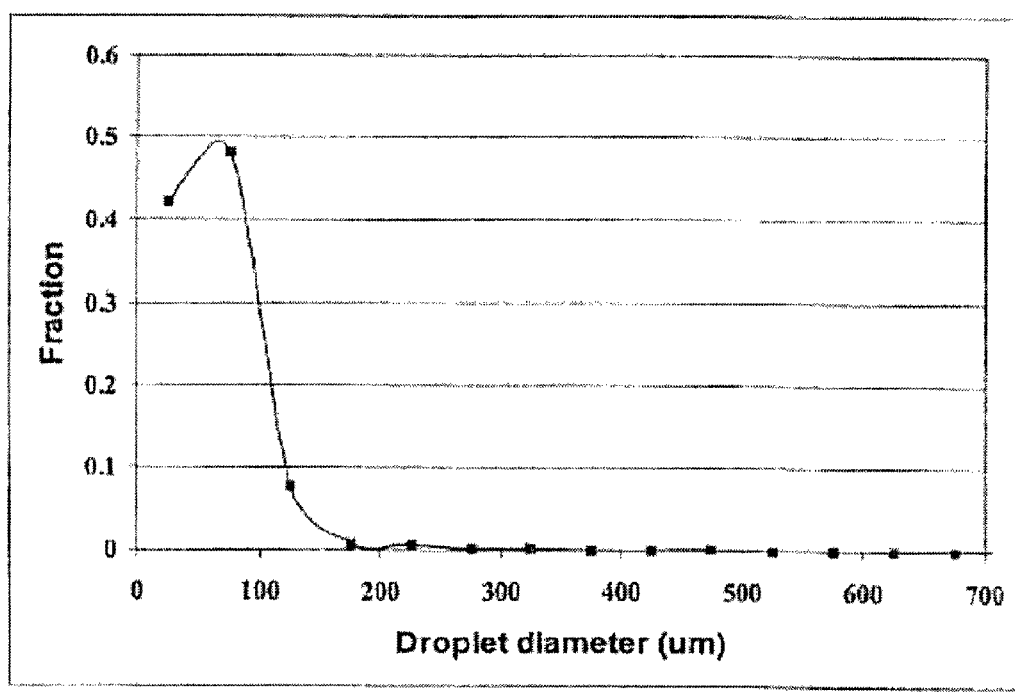
Figure 11:
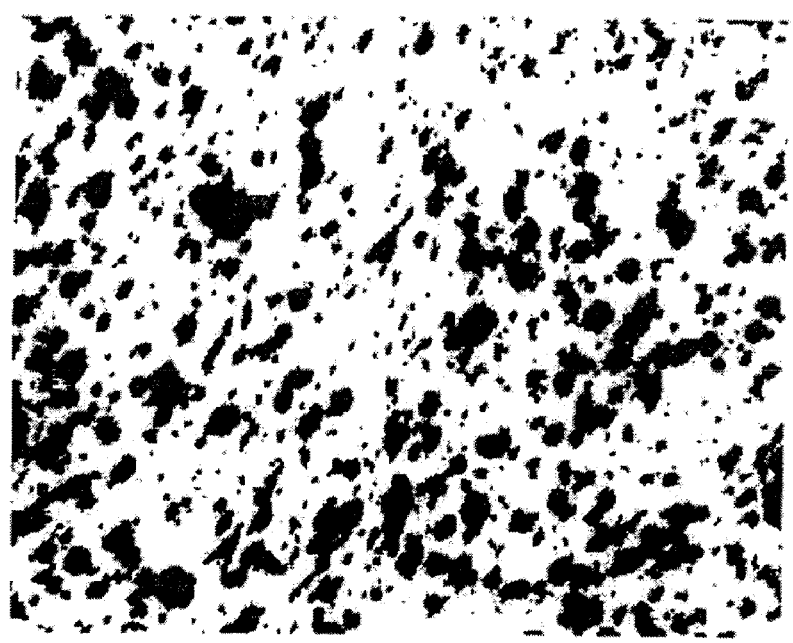
Figure 11:
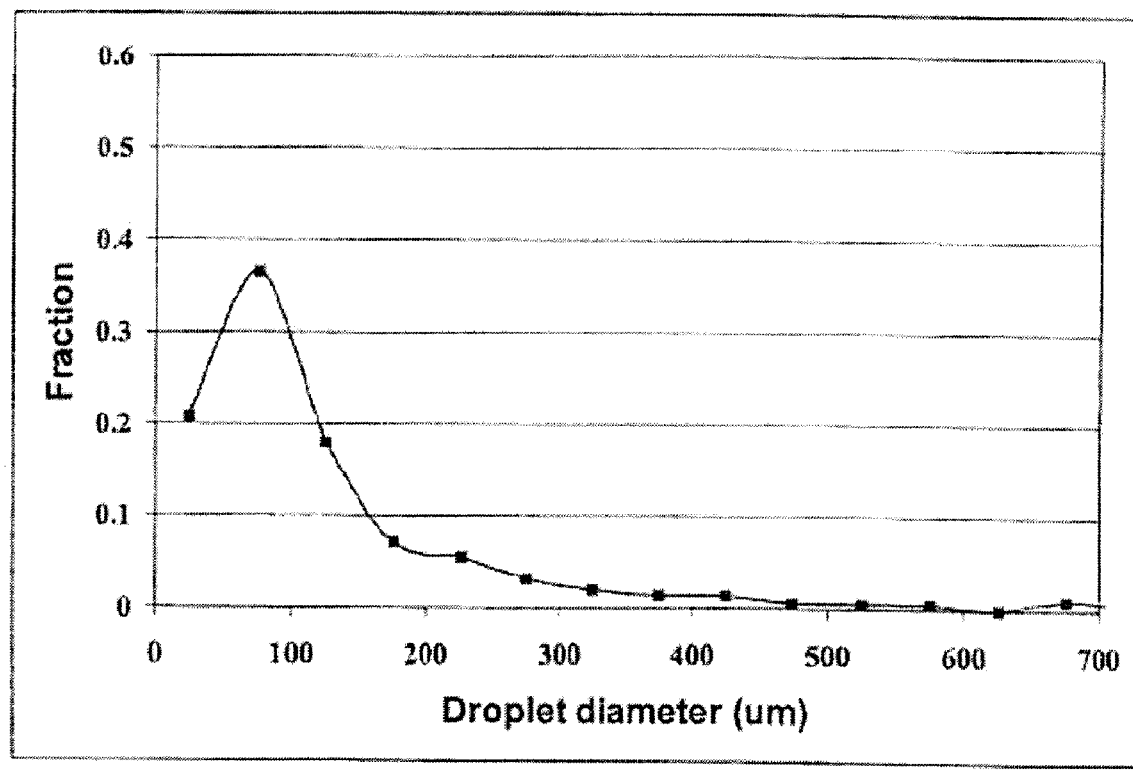
Figure 12:
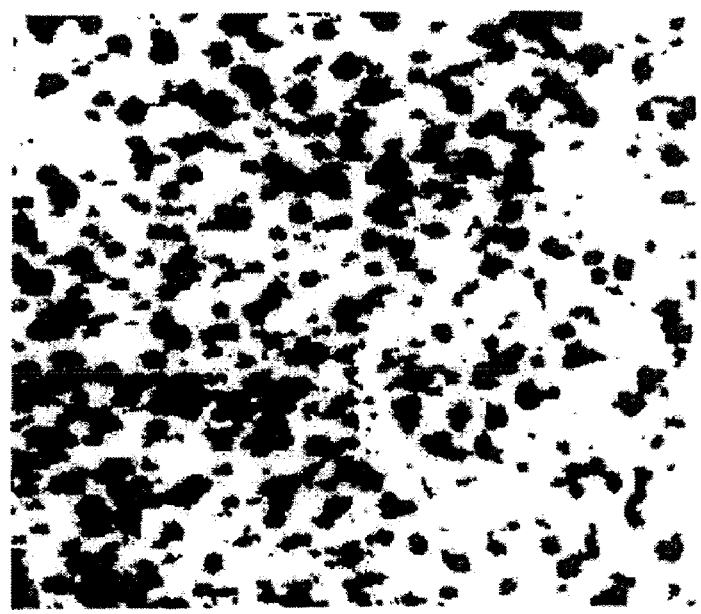
Figure 12:
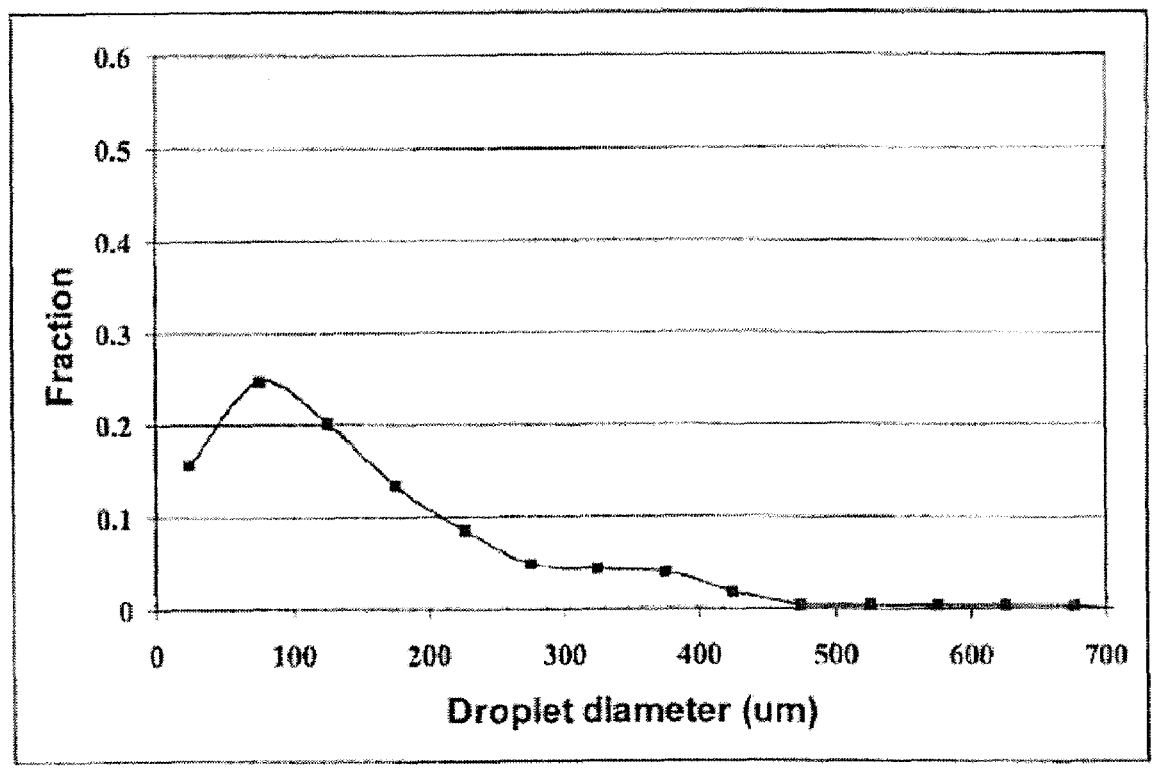

For each of the test fluids, an image of the spray deposit was captured and the resulting droplet size spectra based on number counts of droplet stains in the image was recorded. Specifically, the spray deposition pattern and the droplet size spectra for water is shown in FIG. 10, the spray deposition pattern and droplet size spectra for ethynol is shown in FIG. 11, and the spray deposition pattern and droplet size spectra for the cleaner is shown in FIG. 12. Glycerin, on the other hand, failed to atomize and did not produce a spray at all.

As can be shown in FIGS. 10-12, water had a very small droplet size that was smaller than the droplet size of the ethyl alcohol and smaller than the droplet size of the spray cleaner. The droplet size of the ethyl alcohol was smaller but comparable to the droplet size of the spray cleaner. Thus, as shown in FIGS. 6-9 in comparison to FIGS. 10-12, as the power increased, the droplet size decreased. The glycerin was not atomized by the pump-nozzle combination; the resulting vibration data indicated virtually no vibration in the 4-6 kHz band.

From the deposition images for water, ethynol and spray cleaner, the size distribution of the stains on the target paper were analyzed by image analysis, a common technique used to measure and characterize spray deposition. The number of stains in a representative area of target were categorized by size and counted to produce the results illustrated in FIG. 13.

Figure 13:
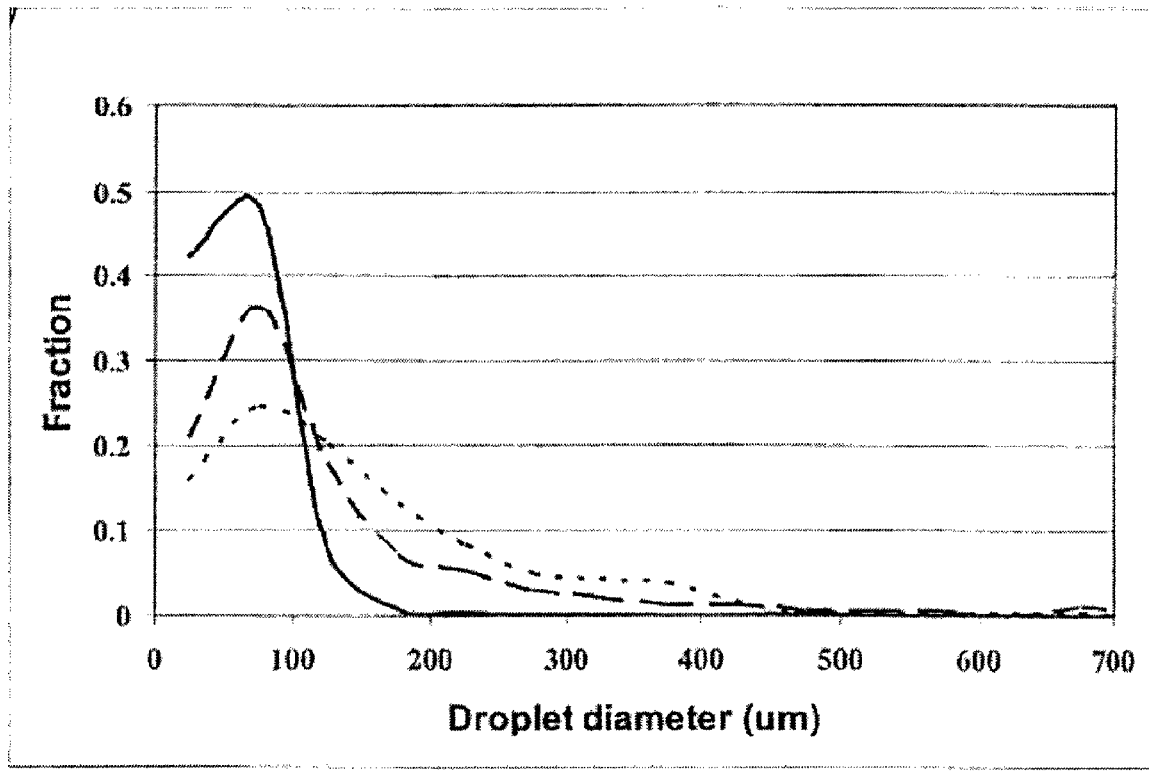
Figure 14:
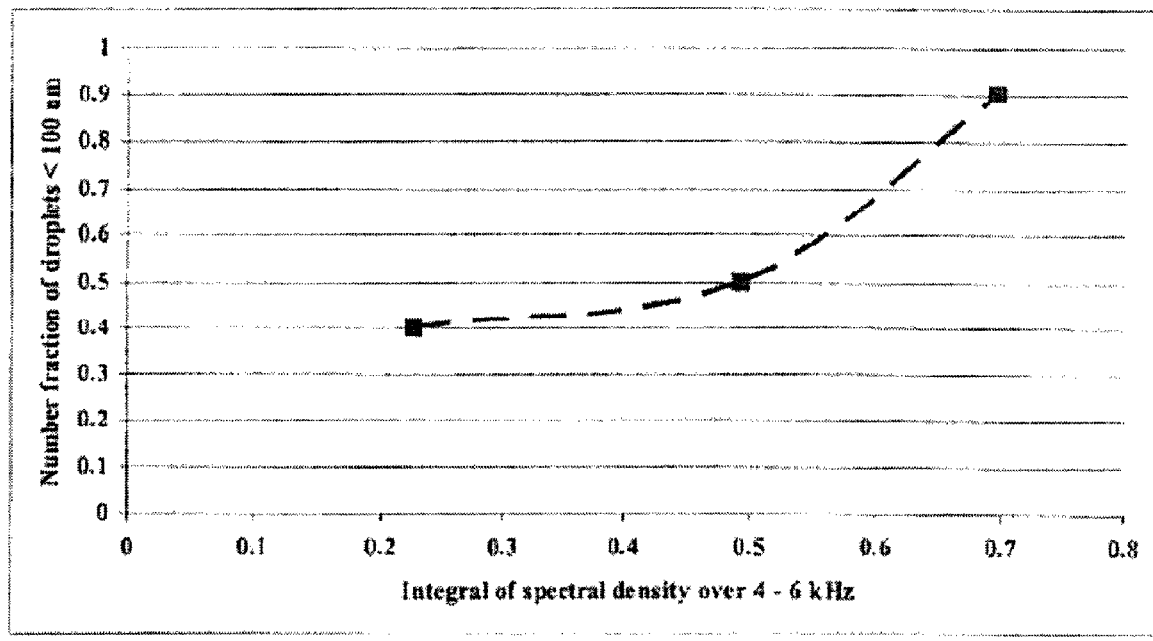

As shown in FIG. 13, from the distribution, the fraction of droplets (by number) below a cutoff size of 100 microns was determined. This number was then compared to the spectral density of the vibrations illustrated in FIGS. 6, 7 and 8. The areas under the vibration curves of the power spectra were integrated over the range of 4-6 kHz, the frequency band most closely associated with the atomization. The relationship between the fraction of droplets and the small size ranges and the total vibration in the 4-6 kHz range is shown in FIG. 14. A strong relationship between vibration and droplet size spectra can be seen.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the disclosure so further described in such appended claims.

What is claimed:

1. A method for determining the atomization characteristics of a fluid being emitted by a nozzle, comprising:
emitting a fluid from a nozzle at controlled conditions including a known flow rate;
sensing vibrations occurring within the fluid nozzle while the fluid is being emitted; and
comparing the sensed vibrations to the vibrations of a known reference fluid having known atomization properties for determining the relative atomization properties of the fluid being emitted from the nozzle.

2. A method as defined in claim 1, wherein the fluid is emitted from the nozzle at varying flow rates according to a predetermined sequence.

3. A method as defined in claim 1, wherein the flow rate is determined by a flow meter.

4. A method as defined in claim 1, wherein the sensed vibrations are converted into a spectral density that is used to calculate a power spectrum, the power spectrum being compared to the power spectrum of the known reference fluid.

5. A method as defined in claim 1, wherein the sensed vibrations are compared to a plurality of known reference fluids, the plurality of known reference fluids including a relatively low viscosity fluid and a relatively high viscosity fluid.

6. A method as defined in claim 1, further comprising selecting a nozzle and operating conditions for emitting the fluid from the selected nozzle in a fluid application process based upon the determined atomization properties of the fluid.

7. A method as defined in claim 6, wherein the fluid application process comprises an agricultural spraying process.

8. A method as defined in claim 6, wherein the atomization properties of the fluid are determined remote from the location of the fluid application process.

9. A method as defined in claim 1, wherein the determined atomization properties of the fluid comprise determining a droplet size of the fluid through the nozzle as a function of flow rate or velocity.

10. A method as defined in claim 1, wherein an accelerometer is used to sense the vibrations.

11. A method as defined in claim 1, wherein the fluid nozzle includes a Z-axis that comprises the direction of flow of the fluid through the nozzle, an X-axis that is perpendicular to the Z-axis and extends to the left and right of the nozzle when facing a front of the nozzle, and a Y-axis that is perpendicular to the Z-axis and the X-axis, the vibrations being sensed in at least the Y-axis direction.

12. A method as defined in claim 1, wherein the sensed vibrations are communicated to a controller that automatically compares the sensed vibrations to the vibrations of the known reference fluid.

13. A system for determining the atomization characteristics of a fluid comprising:
a supply reservoir for holding a fluid, said reservoir including an outlet for dispensing the fluid;
a pumping device for pumping the fluid from the supply reservoir;
a nozzle placed in communication with the supply reservoir for receiving the fluid, the fluid being pumped from the supply reservoir by the pumping device through the nozzle;
a vibration sensor for sensing vibrations occurring within the fluid nozzle as the fluid is being emitted by the nozzle; and
a controller in communication with the vibration sensor for receiving a spray pattern vibration output from the vibration sensor, the controller being configured to compare the sensed vibrations received from the vibration sensor to the vibrations of a known reference fluid having known atomization properties for determining the relative atomization properties of the fluid being emitted from the nozzle, the controller being further configured to control the pumping device for varying the flow rate of the fluid through the nozzle according to a predetermined sequence, the controller being further configured to determine the relative atomization properties of the fluid being emitted from the nozzle as a function of flow rate.

14. A system as defined in claim 13, further comprising a flow meter that determines the flow rate of the fluid as it is pumped from the supply reservoir, the flow meter being in communication with the controller.

15. A system as defined in claim 13, wherein the controller is configured to convert the spray pattern vibration output received from the vibration sensor into a spectral density that is used to calculate a power spectrum, the power spectrum being compared to a power spectrum of the known reference fluid.

16. A system as defined in claim 13, wherein the vibration sensor comprises an accelerometer.

17. A system as defined in claim 13, wherein the controller comprises at least one microprocessor.

* * * * *